United States Patent [19]

Machida et al.

[11] Patent Number: 5,744,097
[45] Date of Patent: Apr. 28, 1998

[54] DNA BASE SEQUENCER

[75] Inventors: Hiroaki Machida; Yuusuke Miyazaki, both of Saitama-ken; Shinichi Takagi, Kounosu; Yoshinori Mishina, Saitama-ken, all of Japan

[73] Assignee: Hitachi Electronics Engineering, Co., Ltd., Tokyo, Japan

[21] Appl. No.: 621,888

[22] Filed: Mar. 26, 1996

[30] Foreign Application Priority Data

Mar. 27, 1995 [JP] Japan .................................. 7-093043
Feb. 23, 1996 [JP] Japan .................................. 8-061904

[51] Int. Cl.$^6$ .................. G01N 15/06; G01N 33/00; C12M 1/00; C12N 15/00
[52] U.S. Cl. .................. 422/68.1; 435/6; 435/287.2; 436/94; 204/456; 935/85; D24/233
[58] Field of Search .................. 435/6, 287.2; 204/450, 204/455, 466; 536/23.1; 935/85; 422/68.1; 436/94; D24/108, 232, 233

[56] References Cited

U.S. PATENT DOCUMENTS 5,164,065 11/1992 Bettencourt et al. ............ 204/299 R

FOREIGN PATENT DOCUMENTS 63-21556 1/1988 Japan .

*Primary Examiner*—Bradley L. Sisson
*Attorney, Agent, or Firm*—Fay, Sharpe, Beall, Fagan, Minnich & McKee

[57] ABSTRACT

The improved DNA base sequencer comprising an electrophoresis plate having a gel electrolyte layer held between two glass plates, one of which is partially cut away on the top edge in the direction of width, an assay compartment for accommodating said electrophoresis plate in a vertically erect position, a lower reservoir of a buffer solution in which the lower part of the gel electrolyte layer in the electrophoresis plate is to be immersed, an upper reservoir of a buffer solution in which the upper part of said electrolyte layer is to be immersed, photoexciting laser light applying means by which laser light is emitted from a lateral side of the electrophoresis plate in such a way that it crosses the lanes in said plate at right angles, and fluorescence detecting means by which the fluorescence emitted from a DNA fragment illuminated with the laser light is picked up and converted to an electric signal, and the apparatus is characterized in that a sharkstoothcomb made of a water-swellable material is inserted from the top edge of said electrophoresis plate into the space between the two glass plates, either the top or bottom edge of said sharkstoothcomb being provided with a plurality of teeth which are each tapered from the root toward the tip. Using this apparatus, samples can be easily and yet positively injected at specified lane positions on the gel electrolyte layer.

13 Claims, 4 Drawing Sheets

DNA BASE SEQUENCER

BACKGROUND OF THE INVENTION

This invention relates to a DNA base sequencer, or an apparatus for determining the base sequences of DNA. More particularly, this invention relates to an apparatus with which the base sequences of DNA can be determined by fluorescent labelling in an efficient and rapid manner.

Gel electrophoresis is practiced extensively as a technique for determining the base sequences of DNA and other proteins. Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescence as emitted upon irradiation with light is being reviewed.

In this method, fluorophore-labelled DNA fragments are caused to migrate through a gel and a light excitation portion and a photodetector are provided for each electrophoresis track in an area 5-20 cm below the start point of electrophoresis. The DNA fragments are assayed as they pass through the line connecting the light excitation portion and the photodetector. A typical procedure of the method is described below. First, using as a template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster it will move and vice versa; this is the principle behind the fractionation of DNA by molecular weight.

Japanese Laid-Open Patent Application (kokai) No. 21556/1988 teaches a DNA base sequencer that is adapted in such a way that a line on the electrophoresis gel at which laser light is applied and the direction in which photodiodes are arranged are both perpendicular to the direction in which DNA fragments migrate in the apparatus. The setup of this apparatus is shown schematically in FIG. 9.

In the apparatus shown in FIG. 9, a laser beam emitted from a light source 70 is reflected by a mirror 72 and launched horizontally from one side of an electrophoresis plate 74 at a predetermined point on the gel. As the fluorophore-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. The fluorescence from each electrophoresis track is condensed by a lens 78 to focus at a light-receiving area 82 in an image intensifier 80. The received signal is amplified and converted to an electric signal in a photodiode array 84 for the purpose of various measurements. The results of measurements are processed with a computer so that the sequences of the individual DNA fragments are calculated to determine the base sequence of the DNA at issue.

As shown enlarged in FIG. 10, the electrophoresis plate 74 comprises a pair of glass plates 86 and 88 between which is held a gel electrolyte layer 90 made of an electrophoresing gel (e.g. polyacrylamide gel). To regulate the thickness of the gel electrolyte layer 90, a spacer 92 is provided between the two glass plates along both vertical edges. The top edge of the glass plate 88 is cut away by a specified depth across the entire width except at both lateral ends. The resulting cutout 94 provides access for a buffer solution to make contact with the top edge of gel electrolyte layer 90. The electrophoresis plate 74 has an overall thickness of about 10 mm but the thickness of the gel electrolyte layer itself is only about 0.3 mm. The upper edge of the gel electrolyte layer is comb-shaped (i.e., has indentations) and located substantially flush with the bottom 96 of the cutout 94. Fluorophore-labelled DNA fragments to be assayed are injected into grooves 75 between the teeth of the comb.

Each of the grooves 75 into which the DNA fragments are to be injected has a width of about 1.5 mm and a depth of no more than about 5 mm. Two grooves are spaced apart by a distance of about 2 mm. Such small dimensions require that a fine glass tube, such as a capillary, be used to inject the samples into the grooves 75. However, due to the transparency of the glass plates and the gel electrolyte, identifying or determining the positions of the individual grooves 75 is extremely difficult and the failure to inject the samples into the right grooves has been frequent.

To determine the base sequences of DNA, the four bases that compose the DNA, i.e., adenine (A), guanine (G), cytosine (C) and thymine (T), must be detected according to the correct order. A failure in sample injection is most likely to cause an error in the result of analysis. Hence, sample injection requires utmost care, which has been one of the reasons for the substantial drop in the operational efficiency.

SUMMARY OF THE INVENTION

An object, therefore, of the invention is to provide a DNA base sequencer that permits easy injection of a sample into a desired lane in the gel electrolyte layer in an electrophoresis plate.

This object can be attained by a DNA base sequencer comprising an electrophoresis plate having a gel electrolyte layer held between two glass plates, one of which is partially cut away on the top edge in the direction of width, an assay compartment for accommodating said electrophoresis plate in a vertically erect position, a lower reservoir of a buffer solution in which the lower part of the gel electrolyte layer in the electrophoresis plate is to be immersed, an upper reservoir of a buffer solution in which the upper part of said electrolyte layer is to be immersed, photoexciting laser light applying means by which laser light is emitted from a lateral side of the electrophoresis plate in such a way that it crosses the lanes in said plate at right angles, and fluorescence detecting means by which the fluorescence emitted from a DNA fragment illuminated with the laser light is picked up and converted to an electric signal, characterized in that a shark's tooth comb made of a water-swellable material is inserted from the top edge of said electrophoresis plate into the space between the two glass plates, either the top or bottom edge of said shark's tooth comb being provided with a plurality of teeth which are each tapered from the root toward the tip.

The shark's tooth comb to be used in the DNA base sequencer of the invention is made of a water-swellable material. If this shark's tooth comb is inserted from the top edge of the electrophoresis plate into the gel electrolyte layer between the two glass plates, it swells upon absorbing the water in both the gel electrolyte layer and the buffer solutions in the upper and lower reservoirs. The swollen shark's tooth comb closes all gaps present between the two glass plates in the electrophoresis plate to ensure that any sample loading zone defined by adjacent teeth of the comb is positively protected against contamination by the samples loaded in other zones.

DETAILED DESCRIPTION OF THE PREFERRED EMBODIMENTS

Figure 1:
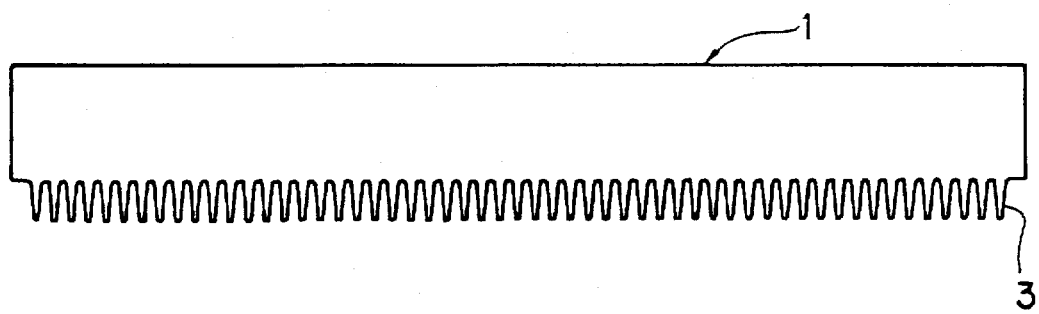
FIG. 1 is a plan view of a shark's tooth comb that is to be inserted for use into the electrophoresis plate in the DNA base sequencer of the invention.

FIG. 1 is a plan view of a shark's tooth comb that is to be used in the DNA base sequencer of the invention. The shark's tooth comb 1 has a series of teeth 3 formed on one of its longer sides. The number of teeth 3 to be formed is in no way limited, but depends on the width of the electrophoresis plate into which the shark's tooth comb is to be inserted.

Figure 2:
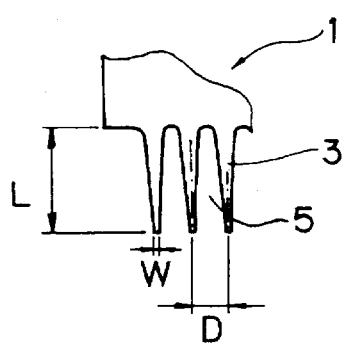
FIG. 2 is a plan view showing partially enlarged the shark's tooth comb of FIG. 1.

FIG. 2 is a plan view showing an enlarged portion of the teeth 3. Each of the teeth 3 is tapered from the root toward the truncated tip to provide a generally trapezoidal shape. Alternatively, each of the teeth 3 may simply be tapered from the root to a pointed tip to provide a generally acute angled triangle. Two adjacent teeth 3 define a space 5 which provides a lane. Given the same length, a shark's tooth comb having tapered teeth 3 provides more lanes than the conventional shark's tooth comb having rectangular (untapered) teeth. The length, L, of each tooth 3 is not limited to any particular value. The distance, D, between teeth 3 also is not limited to any particular value. The values of L and D may be determined as appropriate for the quantity of a sample under electrophoresis analysis, such as fluorophore-labelled DNA fragments, which is to fill the space 5 between adjacent teeth 3. For analysis by gel electrophoresis, about 1.8 μl of the fluorophore-labelled DNA fragment will suffice as a sample to fill the space 5 and a maximum amount of the sample is no more than about 3–4 μl. As guide figures, L and D may be 10.0 mm and 3.5 mm, respectively. The width, W, at the tip of each tooth 3 also is not limited to any particular value. The value of W is determined by the limit of working with a shear blade used in forming the teeth 3 by punching; as a guide figure, W may be about 0.3 mm.

Figure 3:
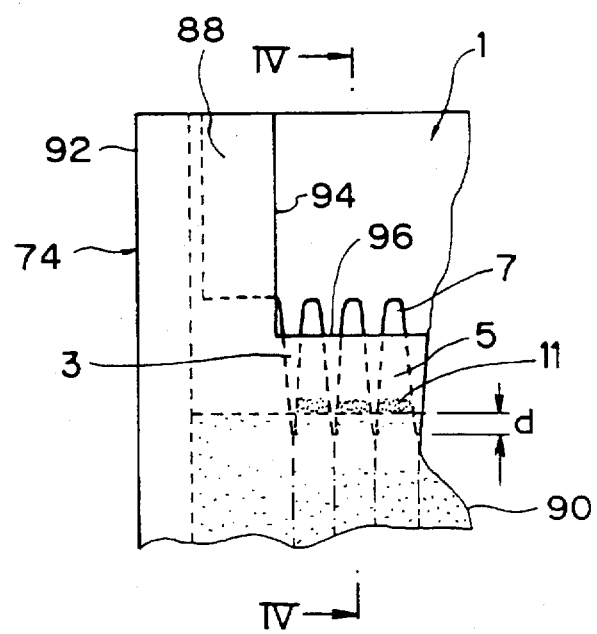
FIG. 3 is a plan view showing partially enlarged the shark's tooth comb of FIG. 1 as it is inserted into the electrophoresis plate.

FIG. 3 is a front view showing partially enlarged the shark's tooth comb 1 as it is set in an electrophoresis plate 74. The shark's tooth comb 1 is inserted between the two glass plates, typically from above the top edge of the electrophoresis plate 74. Preferably, the tips of the teeth 3 of the shark's tooth comb 1 are partly buried to a depth d in the gel electrolyte layer 90. In this way, each tooth 3 serves as a wall that separates two adjacent spaces 5 to be filled with a sample of interest. The value of d is not limited to any particular value; as a guide figure, d may be about 2 mm at maximum.

Figure 4:
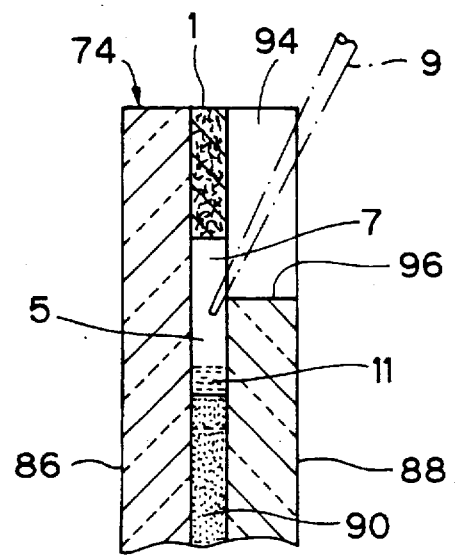
FIG. 4 is a section taken on line IV—IV of FIG. 3.
Figure 5:
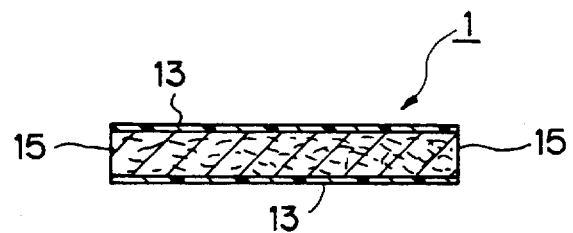
FIG. 5 is a cross section showing schematically a shark's tooth comb laminated with a plastic film on both sides.

FIG. 4 is a section taken on line IV—IV of FIG. 3. As shown, the top edge of the glass plate 88 which combines with the other glass plate 86 to form the electrophoresis plate is partly cut away in the longitudinal direction. Since the teeth 3 have a specified length, an opening 7 is formed between the root of each tooth and the bottom edge 96 of the cutout 94 in the glass plate 88. The tip of injection means 9 such as a capillary or micropipette may be inserted through the opening 7 into the space 5 for injecting a sample 11.

The shark's tooth comb 1 is made of a water-swellable material such as paper, cork, wood, cloth, skin, leather, hide, bamboo or unwoven fabric. Paper is the most preferred. The initial thickness of the water-swellable shark's tooth comb 1 to be inserted between the two glass plates must be less than the distance between the latter. For instance, if the two glass plates are spaced apart by about 0.3 mm, the initial thickness of the shark's tooth comb 1 is preferably from about 0.25 mm to about 0.15 mm. The tips of the teeth 3 of the shark's tooth comb 1 which are buried in the gel electrolyte layer 90 absorb the water in said electrolyte layer, causing the shark's tooth comb 1 to swell until it fills all the gaps between the two glass plates. In order to ensure that the tips of the teeth 3 are positively buried in the gel electrolyte layer 90, the material used to form the shark's tooth comb 1 must have a sufficient strength. To meet this requirement, for example, tissue paper having an initial thickness of about 0.25–0.15 mm has preferably a basis weight in the range from about 150 g/m$^2$ to about 250 g/m$^2$, with the range from about 160 g/m$^2$ to about 180 g/m$^2$ being more preferred.

The paper should not have any adverse effects on the results of analyses. For example, chemically processed pulp or paper that contains fluorophores should not be used. Filter paper or paper used with foodstuffs are preferred since they are extensively used in chemical analyses.

Shark's tooth combs made of paper are prone to tear when they swell upon absorbing water. Tearing has often occurred with swollen paper shark's tooth combs if the surface is scratched by the tip of a sample injecting device such as a capillary. In order to prevent such accidents, the paper shark's tooth comb 1 is preferably laminated with a thin plastic film 13 on both sides. Plastic films suitable for this purpose are films of thermoplastic resins such as polyethylene, polypropylene, nylon, Teflon, poly(vinyl chloride), poly(vinylidene chloride), polybutadiene, polyacrylates, polystyrene and EVA resins. A suitable adhesive (which may be heat- or pressure-sensitive) may be interposed between the paper and the laminating film. The thickness of the film to be used is not limited to any particular value, but it is necessary that the overall thickness of the laminate comprising the paper coated with a plastic film on both sides should be less than 0.3 mm. The thickness of the laminate is variable and ranges typically from 10 to 100 μm, preferably from 20 to 80 μm. To take paper having a basis weight of 160 kg/m² as an example, the thickness of the film to be laminated on both sides is preferably within the range from 30 to 40 μm. Laminating the paper with a plastic film on both sides causes no problems since the cut and exposed faces 15 of the teeth 3 will absorb water to cause the shark's tooth comb 1 to swell.

The gel electrolyte layer 90 is typically formed of 5% polyacrylamide which is a transparent material. The glass plates 86 and 88 are also transparent. Hence, it has been very difficult with the conventional electrophoresis plate to know where the sample should be injected. In contrast, the paper shark's tooth comb to be used in the invention has a white color and the user can readily identify the sites where the sample should be injected. As a result, there will be no errors in sample injection and the operator can provide more sites for sample injection (i.e., lanes) than have been possible in the prior art, thereby increasing the number of samples that can be analyzed on one electrophoresis plate, which contributes to a higher throughput of analysis. It should be noted here that the color of the paper shark's tooth comb to be used in the invention is in no way limited to white and other colors may of course be used as long as they assist in speeding up the process of sample injection.

Figure 6:
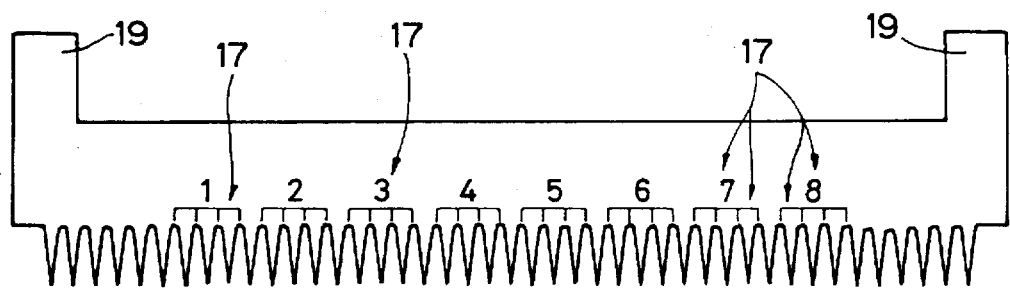
FIG. 6 is a plan view of a shark's tooth comb according to another embodiment of the invention.

As shown in FIG. 6, identifying means 17 may be provided on the surface of the paper to insure that the user can clearly recognize where to inject samples. Such identifying means may typically be provided by printing. For example, numerals or ruled lines may be provided to indicate sample lane groups 1–8, each group consisting of lanes for four bases A, T, C and G. Vertical ruled lines which extend upward from the top edges of the openings 7 are particularly desirable since they not only provide ease in recognizing the positions of the openings 7 but also enable the process of sample injection to be performed in an easy and rapid manner if the tip of injection means such as a capillary is slid along a particular ruled line to be inserted through the opening 7 into the space 5. On the other hand, horizontal ruled lines help identify the boundary between adjacent groups of sample lanes. Numerals and ruled lines may be printed in a monochromatic color such as with a black ink or different colors may be used for different groups. The lanes on either end of the shark's tooth comb are used to inject a liquid having a comparable salt concentration to the sample (the liquid may consist of a reaction buffer, a loading dye and water) in order to insure that the injected sample will be electrophoresed vertically.

Figure 7:
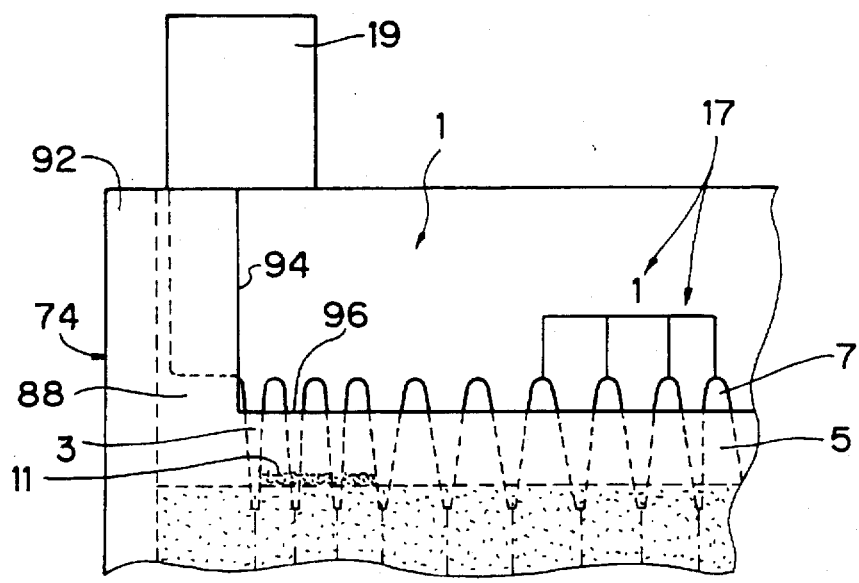
FIG. 7 is a plan view showing partially enlarged the shark's tooth comb of FIG. 6 as it is inserted into the electrophoresis plate.

As also shown in FIG. 6, a pull tab 19 may be provided on both ends of the top edge of the shark's tooth comb 1. As FIG. 7 shows clearly, the pull tabs 19 are desirably long enough to project beyond the top edge of the electrophoresis plate 74 by a sufficient amount such that the user can hold them and pull out the shark's tooth comb 1 from the electrophoresis plate 74. The shark's tooth comb of the invention is used primarily for facilitating sample injection into the respective lanes. Therefore, once the samples have been loaded on the upper part of the gel electrolyte layer for the respective lanes and when they are subsequently advanced into the electrolyte layer, the shark's tooth comb is no longer necessary in the electrophoresis plate. On the contrary, if it continues to be presented in the subsequent stage, the impurities derived from it may potentially affect the result of electrophoresis and/or the presence of the shark's tooth comb itself may prevent uniform application of an electric field to the gel electrolyte layer. To avoid these possibilities, when the injected samples have advanced into the gel electrolyte layer for the respective lanes, the application of voltage is preferably stopped and the shark's tooth comb of the invention is removed from the electrophoresis plate, followed by restoring the voltage application to continue the electrophoresis. Pull tabs 19 are provided to facilitate the removal of the shark's tooth comb before starting electrophoresis with the restored voltage.

The object of the invention cannot be attained if the shark's tooth comb 1 is formed of a plastic material. Thin plastic sheets are subject to local variations in thickness. Also, the spacers and glass plates are also subject to deformations due to warpage. The space between the two glass plates cannot be completely filled with a plastic shark's tooth comb, leaving local gaps between the shark's tooth comb and each of the glass plates. The thickness of the spacers is typically 0.3 mm ±10% whereas the plastic shark's tooth comb has a thickness of 0.324 mm ±10%. Given this tolerance, the electrophoresis plate will have a clearance of up to 0.0864 mm present between the shark's tooth comb and each of the glass plates. This could be solved by improving the surface precision of the glass plates and minimizing the variations in the thickness of the shark's tooth comb. However, this method is not only costly but also impractical for producing large quantities of shark's tooth combs with consistent quality being assured in terms of thickness. It should be particularly mentioned that if gaps occur at the tips of some teeth of the shark's tooth comb, the sample in one space 7 will leak into an adjacent space and the two samples in different lanes intermix to cause an error in the analysis. This problem does not occur in shark's tooth combs made of water-swellable materials. Even if the initial thickness of such shark's tooth comb has local variations or even if the glass plates are deformed due to warpage, the shark's tooth comb will swell upon absorbing water until the space between the glass plates is completely closed. Thus, the use of the shark's tooth comb constructed according to the invention offers the advantage that it allows certain variations in the precision of the shark's tooth comb and other components including the spacers and glass plates without causing any significantly adverse effects on the results of analyses.

Figure 8:
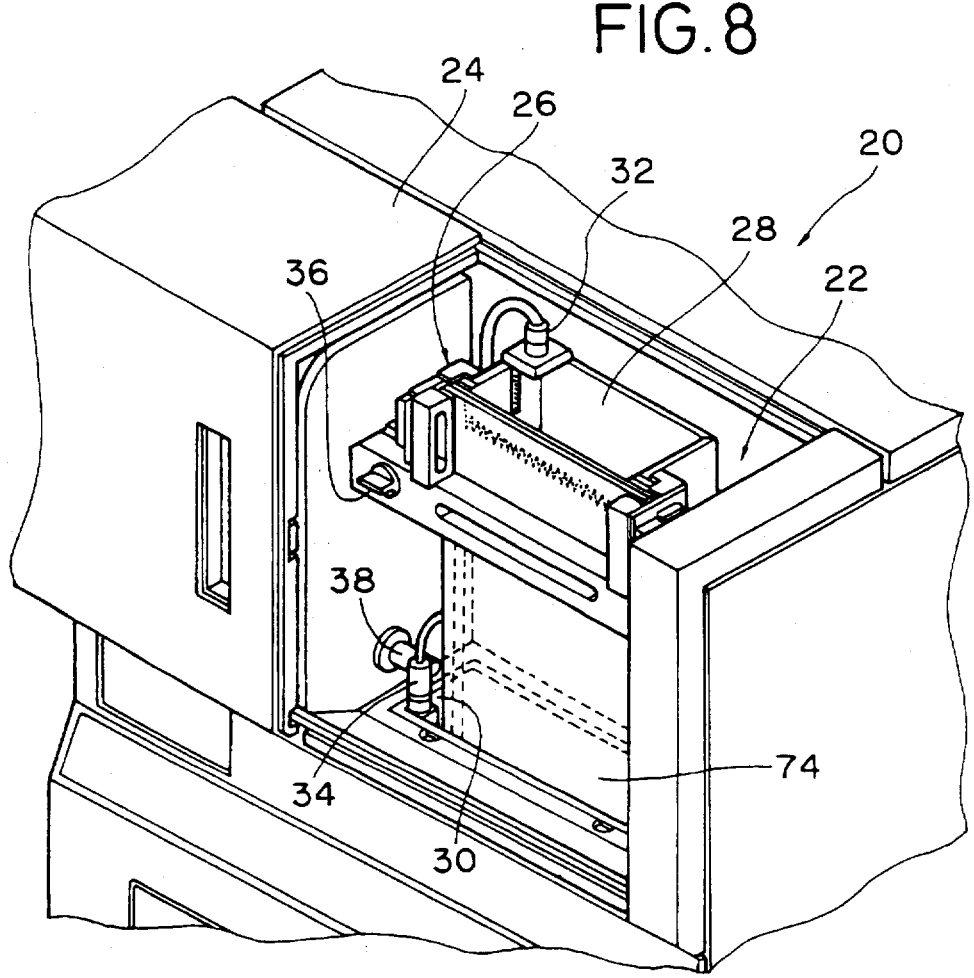
FIG. 8 is a perspective view showing schematically a DNA base sequencer using the water-swellable shark's tooth comb of the invention.
Figure 9:
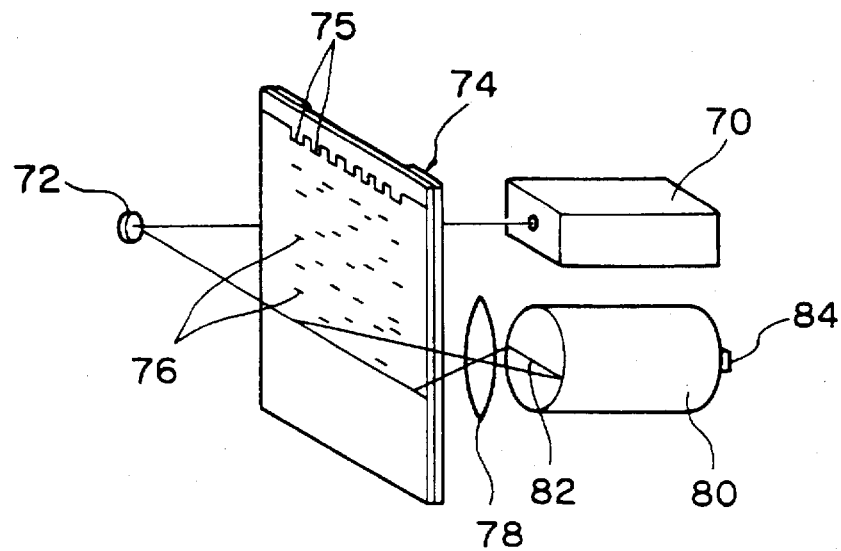
FIG. 9 shows diagrammatically the DNA base sequencer disclosed in Japanese Laid-Open Patent Application (kokai) No. 21556/1988.
Figure 10:
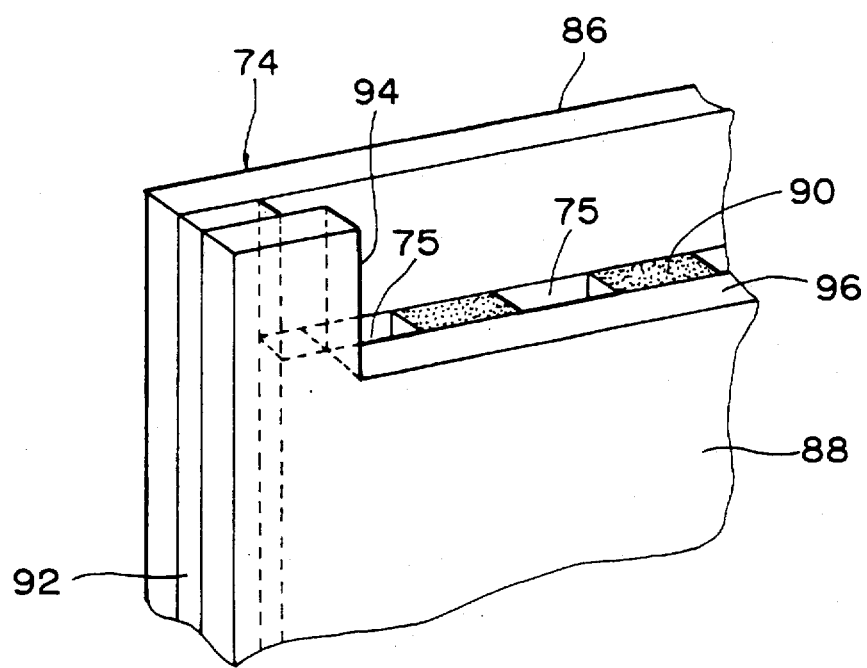
FIG. 10 is a perspective view showing partially enlarged the electrophoresis plate used in the DNA base sequencer of FIG. 9.

FIG. 8 is a perspective view showing schematically a DNA base sequencer using the water-swellable shark's tooth comb 1 of the invention. As shown, the DNA base sequencer generally indicated by 20 has an assay compartment 22 that can be shielded from light by being enclosed with a slidable cover 24 during analysis. The electrophoresis plate 74 is held vertical within the assay compartment by means of a holder 26, which also retains an upper buffer reservoir 28 in such a way that it is integral with the electrophoresis plate 74. The bottom of the electrophoresis plate 74 is placed within a lower buffer reservoir 30. When the upper buffer reservoir 28 is filled with a buffer solution, the latter flows into the electrophoresis plate 74 via the cutout in one of the two glass plates to make contact with the gel electrolyte layer. When the lower buffer reservoir 30 is filled with a buffer solution, the bottom edge of the gel electrolyte layer is immersed in the buffer solution. To ensure that a current will flow from the buffer solution in the upper reservoir through the gel electrolyte layer to the buffer solution in the lower reservoir, electrodes 32 and 34 are connected to the upper and lower buffer reservoirs, respectively. A clamp mechanism 36 is provided to allow for detachable engagement of the electrophoresis plate 74 with the holder 26. A laser light emitting end 38 is provided on a side wall of the assay compartment in such a way that the optical axis of the laser light is perpendicular to the lanes in the electrophoresis plate 74.

As described on the foregoing pages, the shark's tooth comb to be used in the DNA base sequencer of the invention is made of a water-swellable material, so if it is inserted from the top edge of the electrophoresis plate into the gel electrolyte layer between the two glass plates, it swells upon absorbing the water in both the gel electrolyte layer and the buffer solutions in the upper and lower reservoirs. The swollen shark's tooth comb closes all gaps present between the two glass plates in the electrophoresis plate to ensure that any sample loading zone defined by adjacent teeth of the comb is positively protected against contamination by the samples loaded in other zones.

What is claimed is:

1. In a DNA base sequencer including an electrophoresis plate having a gel electrolyte layer held between two glass plates, one of which is partially cut away on a top edge thereof in the direction of width, an assay compartment for accommodating said electrophoresis plate in a vertical position, a lower reservoir of a buffer solution in which a lower part of the gel electrolyte layer in the electrophoresis plate is to be immersed, an upper reservoir of a buffer solution in which an upper part of said gel electrolyte layer is to be immersed, photoexciting laser light applying means by which laser light is emitted from the electrophoresis plate in such a way that the laser light crosses the electrophoresis lanes in said plate at right angles thereto, and fluorescence detecting means by which the fluorescence emitted from a DNA fragment illuminated with the laser light is picked up and converted to an electric signal, the improvement comprising a shark's tooth comb made of a water-swellable paper is inserted from the top edge of said electrophoresis plate into the space between the two glass plates, either the top or bottom edge of said shark's tooth comb being provided with a plurality of teeth which are each tapered from the root toward the tip.

2. A DNA base sequencer according to claim 1, wherein said paper has a basis weight ranging from 150 g/m² to 250 g/m².

3. A DNA base sequencer according to claim 2, wherein said paper has a basis weight ranging from 160 g/m² to 180 g/m².

4. A DNA base sequencer according to claim 1, wherein said paper has exactly two major surfaces laminated with a plastic film, and at least one minor surface on which said paper is exposed.

5. A DNA base sequencer according to claim 4, wherein said plastic film is a polyethylene film.

6. A DNA base sequencer according to claim 4, wherein said paper is laminated on said two major surfaces with a polyethylene film having a thickness of from 30 μm to 40 μm.

7. A DNA base sequencer according to claim 1, wherein said shark's tooth comb has teeth, the tips of which are cut transversely along a straight line.

8. A DNA base sequencer according to claim 1, wherein said shark's tooth comb includes means for identifying a site of sample injection provided at roots of several comb teeth.

9. A DNA base sequencer according to claim 8, wherein said identifying means includes printing symbols and ruled lines on said shark's tooth comb.

10. A DNA base sequencer according to claim 9, wherein said symbols are at least one of numeral and letters, and wherein said ruled lines consist of vertical and horizontal lines.

11. A DNA base sequencer according to claim 1, wherein said shark's tooth comb has a pull tab provided at both right and left ends of a top edge thereof and projecting beyond said top edge.

12. A DNA base sequencer according to claim 1, wherein the tips of the teeth of said shark's tooth comb are buried to a specified depth in the gel electrolyte layer.

13. A DNA base sequencer according to claim 1, wherein said pull tabs project sufficiently beyond said top edge to be grasped by a user.

\* \* \* \* \*